United States Patent [19]

Karger et al.

[11] Patent Number: 5,084,150
[45] Date of Patent: Jan. 28, 1992

[54] SELECTIVE HIGH PERFORMANCE ELECTROKINETIC SEPARATIONS EMPLOYING THE SURFACE OF MOVING CHARGED COLLOIDAL PARTICLES

[75] Inventors: Barry L. Karger, Chestnut Hill; Aharon Cohen, Brookline, both of Mass.

[73] Assignee: Northeastern University, Boston, Mass.

[21] Appl. No.: 566,846

[22] Filed: Aug. 14, 1990

Related U.S. Application Data

[63] Continuation of Ser. No. 374,639, Jun. 30, 1989, abandoned, which is a continuation of Ser. No. 30,225, Mar. 24, 1987, abandoned.

[51] Int. Cl.$^5$ .................. G01N 26/27; B01D 57/02
[52] U.S. Cl. .................. 204/180.1; 264/299 R
[58] Field of Search .................. 204/180.1, 299 R

[56] References Cited

U.S. PATENT DOCUMENTS

| | | | |
|---|---|---|---|
| 3,969,218 | 7/1976 | Scott | 204/180.1 |
| 4,654,132 | 3/1987 | Takagi et al. | 204/182.8 |
| 4,676,897 | 6/1987 | Kuze et al. | 204/180.1 |
| 4,747,920 | 5/1988 | Muralidhara et al. | 204/182.3 |

OTHER PUBLICATIONS

A. Nakamura and M. Muramatsu, "Complex Formation Between N-Dodecyl-β-Alanine and Sodium Alkylsulfate as Reflected in Coadsorption from Mixed Solution," J. Colloid and Interface Sci., 62, 165 (1977).
C. J. Cante, et al., "Surface pH from Electrokinetic Potentials and Titration of Laurate Salts," J. Colloid and Interface Sci., 50, 1 (1975).
R. V. Lauzon and E. Matijevic, "Stability of Polyvinyl Chloride Latex 1. Adsorption of Metal Chelates," J. Colloid and Interface Sci., 38, 440 (1972).
L. H. Allen and E. Matijevic, "Stability of Colloidal Silica 1. Effect of Simple Electrolytes", J. Colloid and Interface Sci., 31, 287 (1969).
K. Shinoda, "The Effect of Added Salts in Water on the Hydrophile-Lipophile Balance of Nonionic Surfactants, The Effect of Added Salts on the Phase Inversion Temperature of Emulsions," J. Colloid and Interface Sci., 32, 4 (1970).
H. Saito, "The Stability of W/O Type Emulsions as a Function of Temperature and the Hydrophobic Chain Length of the Emulsifier," J. Colloid and Interface Sci., 32, 4 (1970).
W. Norde and J. Lyklema, "The Adsorption of Human Plasma Albumin and Bovine Pancreas Ribonuclease at Negatively Charged Polystyrene Surfaces," J. Colloid and Interface Sci., 66, 257 (1978).
J. T. Pearson, "Hydrotropic and Adsorption Properties of Some Bis-Quaternary Ammonium Compounds and Related Cationic Surfactants," J. Colloid and Interface Sci., 37, 509 (1971).

(List continued on next page.)

*Primary Examiner*—John Niebling
*Assistant Examiner*—John S. Starsiak, Jr.
*Attorney, Agent, or Firm*—Weingarten, Schurgin, Gagnebin & Hayes

[57] ABSTRACT

An electrokinetic method for separating molecular species employs the surface of moving charged colloidal particles in a buffered dispersing medium, in a process which combines electrophoresis and a variant of chromatography in which the "stationary phase" surface moves. The colloidal particles have on their surface a material having the ability to interact selectively with the molecular species to be separated. The surface of the particles as originally formed may have such an ability, or the surface is modified to produce it. In one embodiment the colloidal particles are negatively charged and the surface-modifying materials are metal ions. In another embodiment the surface of the colloidal particles is modified by the incorporation of affinity groups. The analytes distribute themselves between the dispersing medium and the surface of the colloidal particles, resulting in analyte migration rates which are functions of the individual distribution equilibrium constants and the rate of colloidal particle migration. A capillary column for conducting the method includes surface-modified charged colloidal particles in a buffered dispersing medium.

13 Claims, 6 Drawing Sheets

OTHER PUBLICATIONS

J. W. Jorgenson and K. D. Lukacs, "Capillary Zone Electrophoresis," Science, 222, 266 (1983).

S. Hjerten, "Free Zone Electrophoresis," Chromatographic Reviews, 9, 122 (1967).

E. A. Hiler, et al., "Electrokinetic Movement of Suspended Colloids in a Flowing Medium," J. Colloid and Interface Sci., 35, 544 (1971).

F. A. Morrison, "Electrophoresis of a Particle of Arbitrary Shape," J. Colloid and Interface Sci., 34, 210 (1970).

P. Bar On, et al., "Electrophoretic Mobility of Montmorillonite Particles Saturated with Na/Ca Ions," J. Colloid and Interface Sci., 33, 471 (1970).

R. H. Ottewill and J. N. Shaw, "An Electrophoretic Investigation of the Behaviour of Monodisperse Polystyrene Lattices in Solutions of Lanthanum, Neodymium, and Thorium Nitrates," J. Colloid and Interface Sci., 26, 110 (1986).

M. J. Sepaniak and R. D. Cole, "Column Efficiency in Micellar Electrokinetic Capillary Chromatography," Anal. Chem., 59, 472 (1987).

P. Gozel, et al., "Electrokinetic Resolution of Amino Acid Enantiomers with Copper(II)-Aspartame Support Electrolyte," Anal. Chem., 59, 44 (1987).

S. Terabe, et al., "Electrokinetic Chromatography with Micellar Solution and Open-Tubular Capillary," Anal. Chem., 57, 834 (1985).

S. Terabe, et al., "Electrokinetic Separations with Micellar Solution and Open-Tubular Capillaries," Anal. Chem., 56, 111 (1984).

R. A. Wallingford and A. G. Erving, "Characterization of a Micro Injector for Capillary Zone Electrophoresis," Anal. Chem., 59, 681 (1987).

B. Feibush, et al., "Chiral Separation of Heterocyclic Drugs by HPLC Solute-Stationary Phase Base-Pair Interactions," J. Amer. Chem. Soc., 108, 3310 (1986).

S. Hjerten, "High Performance Electrophoresis Elimination of Electroendosmosis and Solute Adsorption," J. Chromatography, 374, 191 (1985).

J. N. Kinkel, et al., "Separation of Plasma Membrane Proteins of Cultured Human Fibroblasts by Affinity Chromatography on Bonded Microparticulate Silicas", J. Chromatography, 297, 167 (1984).

K. Shimura, et al., "High Performance Affinity Chromatography of Plasmin and Plasminogen on Vinyl-Polymer Gel Coupled with P-aminobenzamidine", J. Chromatography, 292, 369 (1984).

A. Alpert and F. E. Regnier, "Preparation of a Porous Microparticulate Anion-Exchange Chromatography Support for Proteins," J. Chromatography, 185, 375 (1979).

SELECTIVE HIGH PERFORMANCE ELECTROKINETIC SEPARATIONS EMPLOYING THE SURFACE OF MOVING CHARGED COLLOIDAL PARTICLES

The Government has rights in this invention pursuant to contract Number Che-7918536 awarded by The National Science Foundation.

This application is a continuation of application Ser. No. 07/374,639, filed June 30, 1989 which is a continuation of application Ser. No. 07/030,225, filed Mar. 24, 1987, now abandoned.

FIELD OF THE INVENTION

This invention relates to separation techniques, and more particularly, to an electrokinetic separation method and column employing charged colloidal particles whose surface interacts with molecular species to be separated.

BACKGROUND OF THE INVENTION

Free zone electrophoresis in an open tube or capillary is an emerging technique for separating molecules of biological interest. In this method, the zeta potential on the capillary wall is a minimum. A solution containing the molecules to be separated is placed in an electric field, which causes charged molecules to move toward the electrode of opposite charge at varying rates depending upon their respective charges and sizes.

Electroosmosis is the name given to the phenomenon involving bulk solvent migration in an electrophoresis experiment conducted in a capillary possessing charge on its inner surface. The bulk solvent flow is toward the electrode having the same charge as the capillary wall and results from migration of hydrated counterions corresponding to the charges on the capillary surface. In the case of a negatively charged capillary, these hydrated counterions move toward the negative electrode when the system is placed in an electric field, carrying the bulk solvent along with them.

Electrophoresis is generally applicable to the separation of charged materials provided only that their electrophoretic mobilities are sufficiently different from each other. Thus, electrophoresis has been applied to the separation of such materials as proteins, nucleic acid components, and cells. Many materials of biological interest are charged in solution, and although electrophoresis can in principle be used to separate them, some such materials have very similar electrophoretic mobilities and hence are poorly separated.

Electrophoresis of charged colloids is known. See for example the symposium papers published in "Modern Trends of Colloid Science in Chemistry and Biology," International Symposium on Colloids and Surface Science, 1984, Edited by Hans Friedrich Eicke, Brikhauser Verlog, 1985.

Electrokinetic separation of uncharged solutes via partitioning of such solutes between charged micelles of sodium dodecyl sulfate and the surrounding dispersing medium has also been accomplished. As used herein, "partition" means liquid-liquid distribution of a species between the dispersing medium and the interior of a micelle. See for example the papers by Terabe, et al., in Analytical Chemistry, 57, 834-841 (1985); and Analytical Chemistry, 56, 111 (1984). In this technique, the bulk solvent movement toward the negative electrode caused by electroosmosis sweeps the negatively charged micelles of SDS toward this electrode in spite of their tendency to move toward the positive electrode by electrophoresis. The neutral species to be separated partition themselves between the dispersing medium and the interior of the micelles, and hence move toward the negative electrode at rates which respectively depend upon their distributions between the micelles and the medium. Molecules which do not partition into the micelles move toward the negative electrode at the bulk solvent flow velocity.

A paper by P. Gozel, et al., in Analytical Chemistry, 59, 44-49 (1987), extended Terabe's work to the separation of racemic mixtures of derivatized amino acids, employing diastereoisomeric copper II complexes and micelles of sodium tetradecyl sulfate. Other recent papers have also dealt with electrokinetic separations involving micelles. See, for example, the paper by M. J. Sepaniak and R. O. Cole, Analytical Chemistry, 59, 472 (1987).

An alternative separation method widely used today is adsorption chromatography. In this technique, resolution is based on differences in the extent of adsorption of molecules on various surfaces. Today, tailor-made surfaces can be employed for separation of closely related species such as optical isomers (B. Feibush, et al., J. Amer. Chem. Soc., 108 3310-3318 (1986)) and oligonucleotides of a common base number but different sequence. In addition, high selectivity can be achieved using biospecific adsorption such as affinity chromatography.

The fields of capillary electrophoresis and modern adsorption chromatography have up to now not been combined. Each has advantages, e.g., electrophoresis provides high efficiency, while adsorption chromatography provides high selectivity by the use of specifically-chosen adsorptive surfaces.

In view of the importance of biochemistry and biotechnology in medical research and in the production of myriad materials of pharmaceutical or biological interest, as well as the ever-increasing demands placed on analysts working in such fields as environmental and industrial chemistry, it is of great interest to the scientific community to have improved procedures and tools for separating complex mixtures of molecular species. The present invention combines the efficiency of capillary electrophoresis and the selectivity of adsorption chromatography for high performance separations.

SUMMARY OF THE INVENTION

The need for improved methods and techniques for separating complex mixtures of molecular species is addressed in the present invention, which provides a highly sensitive, efficient, and selective method for separating complex mixtures of materials. A capillary column containing colloidal material for carrying out such separations is also disclosed. The separating method and capillary column to be described below offer the advantages of rapid high resolution separations of complex mixtures of materials using very small sample sizes, while simultaneously providing an extremely high and adjustable selectivity so that separations of the molecules of particular interest can be readily optimized.

The invention provides an electrokinetic method of separating molecular species, in which colloidal particles are provided in a dispersing medium containing a buffer, and the surface of the colloidal particles possesses the ability to interact with at least one of the molecular species to be separated. The colloid and its buffered dispersing medium are placed in a capillary tube, and an aliquot of a sample mixture containing the molecular species to be separated is injected into the capillary tube with the result that the species to be separated distribute themselves between the dispersing medium and the colloidal surface. An electric field is imposed across the length of the capillary tube, causing a separation of the analytes to occur, and the separated materials are finally detected.

The surface of the colloidal particles is employed in its original state provided it has the required interacting capability, or is modified appropriately, for accomplishing a particular separation, by incorporation thereon of chemical functional groups or by addition thereto of material which can interact with species to be separated. In one example of this process, the surface of negatively charged colloidal particles is modified by the addition of positive ions of at least one metal having the ability to interact with the species being separated. In another embodiment, the colloids surface is modified by the incorporation thereon of affinity groups. It is to be emphasized that the foregoing are only a few of many possible examples of the invention.

A capillary column for carrying out the above-described electrokinetic separation of molecular species includes a 0 capillary tube containing colloidal particles in an electrically-conductive dispersing medium, and at least one material having the ability to interact with the molecular species to be separated, this material being located at least in part on the surface of the colloidal material, thereby modifying that surface. Where the colloidal particles as formed have a surface with the requisite interacting ability, however, no further surface-modifying material is necessary.

DESCRIPTION OF THE DRAWING

The invention will be better understood from a consideration of the following detailed description taken in conjunction with the solely exemplary drawing in which.

DETAILED DESCRIPTION

Figure 1:
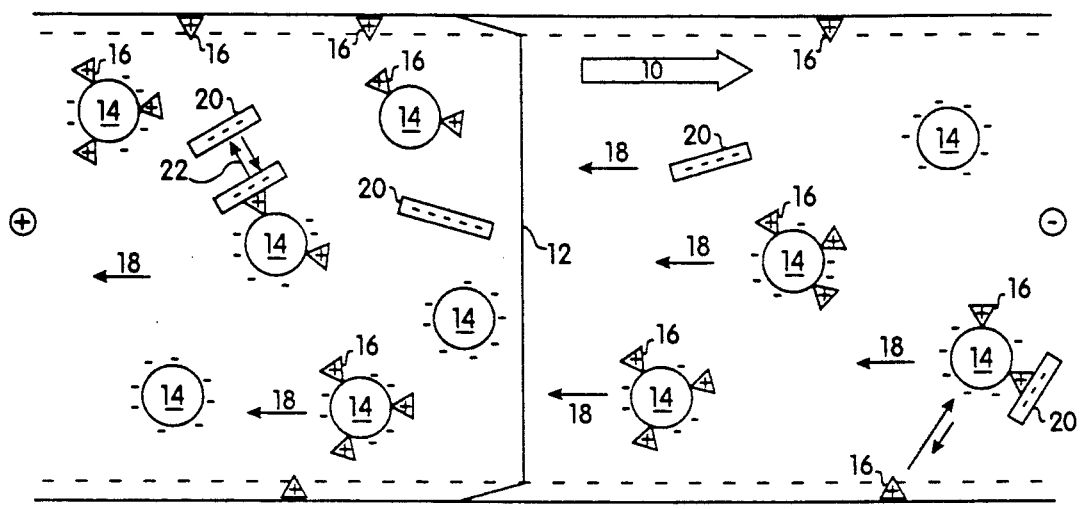
FIG. 1 shows a schematic diagram of the proposed mechanism for one variant of the separating method, illustrated for a system containing negatively charged colloidal particles, negatively charged analytes, positively charged complexing agents, and a fused silica capillary.

As used in this document, the terms "colloidal material" and "colloidal particles" mean particles of solid material or groupings of molecules surrounded by a liquid dispersion medium. The phrases thus include both sols and micelles. The phrase "affinity group" means any chemical functional group or molecule which has an affinity for another sort of functional group or molecule, so that when the affinity group contacts material with which it has affinity, complexation or adsorption occurs.

The present invention is an electrokinetic method of separating molecular species, and a corresponding capillary electrophoresis column in which the method is carried out. The key to the success of the separation method is the use of the surface of colloidal particles to mediate the separation.

The electrokinetic separation method of the invention is carried out by providing a dispersion of charged colloidal particles in an electrically-conductive medium in a capillary tube, the surface of the colloidal particles being capable of interacting chemically with at least one molecular species. An aliquot of a mixture containing a plurality of molecular species to be separated, and including the molecular species with which the colloidal surface is capable of interacting, is placed into the colloidal dispersion in the capillary, an electric field is imposed across the capillary, and the separated molecular species are detected as they traverse the capillary.

Sols and micelles comprise the colloidal particles useful in the method and capillary of the invention. The charge on the colloid is due to the presence of charged functional groups on the colloidal surface and is either inherently present on the colloid as formed or is produced by suitable modifications of the initially-formed colloidal material to incorporate such charged functional groups, such modifications being known to those skilled in the art. Depending on the particular configuration employed, the charge on the colloidal particles may be either positive or negative.

The surface of the colloid particles is capable of interacting with one or more of the molecular species to be separated. If it does not possess this property as originally formed, the surface is suitably modified by adding to it at least one material having the ability to interact selectively with the molecular species to be separated. The material added to the surface of the charged colloidal particles may be neutral in charge provided that it fulfills the requirement of being able to interact with the molecular species being separated, or it may be charged, the charge generally being opposite to the charge on the species being separated. The modifications of the colloidal surface are accomplished either by incorporating chemical functional groups into or onto the colloidal surface, generally before the colloidal material is placed in the capillary, or by adding to the dispersing buffer-mobile phase one or more complexing materials which adhere to and modify the colloidal surface. Examples of functional groups useful in the invention are the so-called "affinity groups" employed in affinity chromatography, while positive metal ions provide an example of adhering additives in the mobile phase.

Sample injection is conducted by siphoning a small amount of sample into the capillary, or by electroinjection, both of these techniques being well known to those skilled in the art. For details on injection techniques see the articles by (a) S. Terabe, et al., Analytical Chemistry, 57, 834–841 (1985); (b) J. W. Jorgenson and K. D. Lukacs, Science, 222, 266–272 (1983), and (c) R. A. Wallingsford and A. G. Erving, Analytical Chemistry, 59, 681 (1987), these articles being hereby incorporated by reference.

Imposing an electric field across the capillary tube causes a separation of the analytes to occur. The potential field to be employed in carrying out the separating method is a function of the length of the capillary used. Typically a minimum of 50 volts per cm and a maximum of 500–600 volts per cm is employed. It is desirable to minimize the current which flows through the capillary to minimize Joule heating effects. This is accomplished by employing appropriate concentrations of buffer, and/or by using buffers having relatively low conductivities. Such current regulation is known to those skilled in the art. Buffers and their use are discussed in the book "Buffers for pH and Metal Ion Control," by D. D. Perrin and B. Dempsey, published by Chapman and Hall, London (1974). Cooling of the capillary column while it is in use is preferred for good reproducibility. Such cooling may be accomplished in any of the ways known to the art, for example, by circulation of constant temperature air or by circulation of a constant temperature liquid through a jacket surrounding the capillary column.

The electrophoresis equipment to be employed in carrying out the process of the invention, in particular, the power supply for use in imposing the electric field across the capillary and the detector for use in detecting the separated molecular species, are known and are commercially available from several instrument manufacturers.

The capillary column of the invention includes a capillary containing charged colloidal particles in an electrically-conductive medium, and a material capable of interacting with molecular species to be separated, this material being located on the surface of the colloidal particles and being present on the colloid as formed or as a result of subsequent additions to or modification of the colloidal surface.

The capillary normally has a length in the range of 10–100 cm from the injection end to the detector, but the actual capillary is somewhat longer than this to permit the detector end to reach the conducting buffer reservoir. It generally has an internal diameter of 25–150 microns. For most purposes, the preferred dimensions are 40–80 cm in length and 50–100 microns internal diameter. Fused silica is the preferred material of construction, though capillaries of other materials such as glass, alumina and beryllia may also be employed.

Silica normally has negative charges on its inner surface. However, if a positively-charged inner surface is desired, this can be produced by coating the surface with a layer of a positively-charged material such as polyethylenimine, as is known to the art. In this regard, see the article by A. J. Alpert and F. E. Regnier, J. Chromatography, 185, 375–392 (1979), which is hereby incorporated by reference. In the event that a capillary having an essentially uncharged surface is desired, for example, if free zone electrophoresis is to be conducted, the capillary may be treated as disclosed by S. Hjerten in J. Chromatography, 374, 191–198 (1985), which is hereby incorporated by reference.

The colloidal particles referred to may be either solid particles or micelles. Many sorts of each type of colloidal particle are known to the art. A representative but not exhaustive list of suitable micelle materials is: long chain alkyl sulfates such as decyl sulfates, $CH_3(CH_2)_{9+n}OSO_3M$ where $n=1$ through 8 and M is lithium, sodium, or potassium; ammonium salts of long-chain alkyl amines such as methonium bromides $Br^-(CH_3)_3N^+(CH_2)_nN^+(CH_3)_3Br^-$ in which n is 6 through 18; long-chain alkyl benzene sulfonic acids such as decylbenzenesulfonic acids, $CH_3(CH_2)_{9+n}C_6H_4SO_3M$ in which $n=1$ through 18 and M is lithium, sodium, or potassium; long-chain alkyl-substituted anilines such as decyl anilines $CH_3(CH_2)_{9+n}C_6H_4NH_2$ in which n is 1 through 8; and decyltrimethylammonium bromides $CH_3(CH_2)_{9+n}N^+(CH_3)_3Br^-$ in which n is 1 through 8.

Sodium and potassium dodecyl sulfates are preferred micelle-forming materials. The micelle-forming material is employed at a concentration generally between the critical micelle concentration for the particular material and several times this critical micelle concentration. It will be appreciated by those skilled in the art that the concentration of the micelle-forming material, so long as this concentration is above the critical micelle concentration, affects the number, shape, surface area, and volume of the micelles produced in the system.

A representative but not exhaustive list of classes of solid particulate colloidal materials is: polyacrylamides, polyacrylic acids, polyacrylonitriles, polyamides, polyesters, polycaprolactams, polycaprolactones, polycarbonates, polysiloxanes, polyethyleneoxides, polyimines, nylons, polyimides, polystyrenes, polysulfones, polyolefins such as polyethylenes, polypropylenes, and polybutadienes, and polymers of vinyl monomers, such as poly(vinylchloride) and poly(vinylalcohol), and kaolin.

Polystyrene is a preferred type of solid particulate colloid which may be employed in the invention, because it is readily available and because its surface may readily be modified in a variety of ways known to those skilled in the art, to produce either positively or negatively charged functional groups. Examples of other preferred solid particulate colloidal materials are silica and poly(vinylchloride). The concentration of solid particulate colloids to be employed depends on the sizes of the particles, their charges, and the surface area desired.

The buffer provides a conductive path for the electrical circuit and also controls the charges on various segments of the system. It is generally selected to have a low conductivity to minimize the current and thereby to minimize Joule heating effects. Tris borate and phosphate buffers are preferred. Other possible buffers include but are not limited to HEPES and acetate buffers.

Any material which he attached to the surface of the colloidal particles and which can in turn interact with the molecular species being separated may be employed as the surface-modifying agent. Chemical functional groups such as "affinity groups" employed in affinity chromatography are one example of surface-modifying materials, as are materials which adsorb to the colloidal surface, such as metal ions.

A representative but not exhaustive list of chemical functionalities which can be attached to the surface of the colloidal particles to provide this surface with the ability to interact with molecular species being separated follows; the material each type of functionality interacts with is shown in parentheses: antibodies (antigens); antigens (antibodies); oligonucleotides (complementary oligonucleotides); anions such as $-CO_2^-$ (cations such as $-^+NH_3$); concanavalin A (glycoproteins); p-aminobenzanmdine (plasmin); metal salts of ATP (adenylatekinase).

Where the colloidal particles are negatively charged, positively charged surface-modifying agents are desirable. Any metal may in principal be employed to modify the surface of negatively charged colloidal particles, but metals having biological importance such as the transition metals, the alkali metals, the alkaline earth metals, and the lanthanides are preferred. Representative transition metals useful in the invention are copper, iron, zinc, and nickel, while representative alkaline earth metals are calcium and magnesium.

In the case of metal additives in the buffer, negatively charged colloidal particles are preferred for the separation of negatively charged species because it then becomes possible to modify the surface of the colloidal particles conveniently by means of the addition of any of a wide variety of positive metal ions, which in turn have different selectivities with respect to various possible analytical species to be separated.

An alternative embodiment of the invention employs the same concepts but with each element of the opposite charge. In particular, it is possible to separate positive species by the method of the invention employing a capillary containing positively charged colloidal particles. For example, an alkyl ammonium salt of a long chain amine can be chemically bonded via the alkyl chain to a colloid or adsorbed onto hydrophobic colloidal particles, producing a positively charged surface on the particles. The particle surface can be employed for separations of negative species directly, can be further modified by the addition of negative materials capable of interacting with particular positively charged analytes, or can be further modified to contain affinity groups. It is also possible to employ neutral colloidal surface-modifying agents, provided that they are able to interact with the analytical species to be separated and do not reduce the charge on the colloid significantly.

In carrying out the separation method of the invention, an appropriate capillary is selected and one end is attached to a suitable detector, a mixture of buffer and colloidal particles having an appropriately-active surface is prepared, the capillary is filled with the colloid in buffer solution with the ends of the capillary being maintained in the buffer solution, a small aliquot of sample is injected into the front end of the capillary, and electrophoresis is carried out in the normal fashion.

In addition to use of the method and capillary column of the invention in qualitative and quantitative analysis of complex mixtures, it is also possible and advantageous to carry out micropreparative separations by collecting appropriate fractions as the separated materials exit the capillary column. Each peak consists of colloidal particles and a single desired analyte. The analytes are separated from the colloidal material either on-line or off-line by methods known to the art. See, for example, L. Johansen et al., J. Imm. Methods, 59, 255-264 (1983); and J. L. Millain et al., Clin. Chem., 31, 54-59 (1985).

Although the best separations are achieved using charged colloidal particles having a surface which is capable of interacting with one or more of the molecular species to be separated, those skilled in the art will realize that uncharged particles may also be employed, in electroosmosis—based purification procedures. For example, uncharged colloidal particles whose surface bears uncharged affinity groups will adsorb molecular species which complex with these affinity groups, and uncharged particles whose surface as formed can interact with and adsorb particular molecular species will adsorb such species. Even if the resulting complex is uncharged, it will move with other uncharged materials at the bulk flow rate, separating from charged materials. Subsequent separation of colloidal material from noncolloidal material followed by a desorption step effects a purification of the adsorbed material from the remaining materials.

It is believed that the interaction of the colloidal surface with molecular species being separated mediates the movement of the separating species in any of several ways, depending on the particulars of each case. The following comments are offered only as aids in understanding the invention, the Applicants not wishing to be bound by any of the particular theories advanced.

To the extent that separating species are associated with the colloidal surface they move through the capillary with the colloid. In the case of free zone electrophoresis, in which the capillary inner wall is essentially neutral, the electrophoretic mobility and Possibly the direction of motion of the separating species are changed from those of the unassociated analytes. For the case of a combination of electrophoresis and electroosmosis operating simultaneously in a capillary having a charged inner wall, the separating species will tend to migrate through the column more slowly than they otherwise would, and in a direction which depends on whether electrophoresis or electroosmosis dominates. In all cases, the surface of the colloidal particles interacts with analytes like the stationary phase of the chromatographic column, but as the invention combines chromatography and electrokinetic separation principles, this "stationary" phase moves at a fixed rate.

As one example, for the case of a fused silica capillary, negatively charged colloidal particles, positively-charged surface-modifying species such as metal ions, and a mixture of negatively charged species such as oligonucleotides to be separated, the situation is believed to be generally as illustrated in FIG. 1. The fused silica capillary has negative charges on its surface. The counter ions corresponding to these surface charges are hydrated in solution and migrate toward the negative electrode as shown by arrow 10 upon application of an electric field across the length of the capillary. This is electroosmosis, discussed above, and produces a very uniform osmotic flow profile 12 as is known to those skilled in the art. Negatively charged colloidal particles 14, are present in the buffered dispersing medium (medium not shown). These move toward the negative electrode by electroosmosis because of bulk solvent flow, but are slowed by their tendency to move toward the positive electrode by electrophoresis. The net result is that such anionic particles move toward the negative electrode, but move in this direction more slowly than uncharged molecules would move by electroosmosis. If positively-charged complexing agents 16 are on the surface of the colloidal particles, the electrophoretic migration of the particles may be altered. Solute molecules that can interact with the complexing agent on the colloidal surface will now migrate in the electric field as a function of their distribution between the surface of the colloid and the medium.

The direction of electrophoretic migration of negative species is shown by arrows 18. Upon addition of a mixture of negatively charged analytes such as oligonucleotides 20, which can interact with the complexing agent 16 on the surface of the colloidal particles, these analytes 20 distribute themselves between the modified colloidal surface and the buffered dispersion medium as shown by equilibrium 22. The equilibrium constant for the complexation of any given analyte 20 with a modified colloidal surface is different from that of other analytes, depending on such factors as the shape, size, and charges on the analytes. Because of the distribution of the analytes between the bulk solution and the colloidal surface, each type of analyte will move at a rate determined by the amount of time it spends attached to the colloidal particles. As the charged colloidal particles move only slowly toward the negative electrode, the analytes thus move slowly toward the negative electrode. With the resulting large "time window" for separations, small differences in overall migration rates of different analytes can produce separations. Factors which affect the differential retention include the amount and type of charge on the species involved, the material modifying the surface of the micelle, the temperature, the pH, etc.

As another example, affinity groups could be covalently attached to the surface of solid colloidal particles while still maintaining sufficient charge for electrophoretic migration of the colloid. The affinity groups could then selectively adsorb their complement by the principle of biospecific recognition. The complement molecules would then migrate with the colloid.

EXPERIMENTAL SECTION

The invention will be further clarified by a consideration of the following examples, which are intended to be purely exemplary of the invention.

Apparatus

Figure 2:
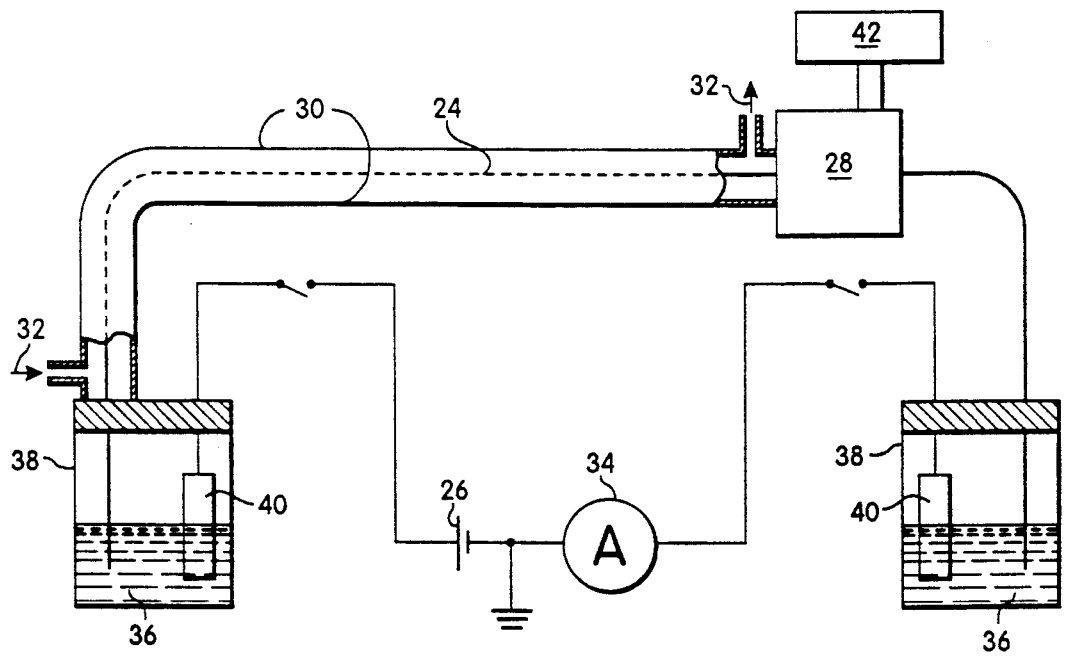
FIG. 2 shows a diagram of the equipment employed in carrying out separations using the method and capillary column of the invention.

The experimental setup employed is shown in FIG. 2. Electrokinetic separation of oligonucleotides was performed in fused silica tubing 24 of 0.05 mm ID (Scientific Glass Engineering, Ringwood, Victoria, Australia) with various column lengths from 500–850 mm, depending on the experiment. A regulated high voltage D.C. power supply 26, Model LG-30R-5 (Glassman, Whitehouse Station, N.J.) which could deliver high voltage up to 30 kV was used to produce the potential across the capillary. A UV detector 28 was employed (Soma S-3702, IR&D, Kingston, Mass.). This detector was modified as described in the article by Terabe, S., et al., Analytical Chemistry, 56, 111-113 (1984), which is hereby incorporated by reference. The tubing was thermostated at 25° C. using a liquid cooling system (Lexacal Model EX-100DD with FTC-350A, Neslab Instruments, Inc., Portsmouth, N.H.) for the oligonucleotide separations. Cooling fluid from this unit was circulated through a manifold 30 surrounding capillary 24 as shown by arrows 32. An amperometer 34 monitored the current in the circuit. Each end of the capillary was immersed in buffer solution 36 contained in buffer reservoirs 38. Each buffer reservoir also contained a platinum electrode 40 connected to power supply 26. A Nelson Analytical Model 762SB A/D interface (Cupertino, Calif.) attached to an IBM PC/XT 42 was used to record the electropherograms and to process data for the oligonucleotides.

Materials

Sodium dodecyl sulfate (SDS) was of protein research grade (Nakara Chemicals, Kyoto, Japan, or Schwarz/Mann Biotech, Cambridge, Mass.). The lower molecular weight polythymidines (up to 6 bases) were purchased from Sigma Chemical Co. (St. Louis, Mo.); higher molecular weight oligonucleotides were synthesized using an Applied Biosystems 380A DNA synthesizer (Foster City, Calif.).

The water was deionized and triply distilled. The other reagents were A.R. purity grade. All buffer solutions were filtered through a Nylon 66 filter unit of 0.2 $\mu$m pore size (Schleicer and Schuell, Keene, N.H.). The oligonucleotide samples were kept frozen at $-20°$ C., and working sample solutions were stored at 4° C.

Procedure

Capillary tubes were filled with the desired buffer using a 100 $\mu$L gas tight syringe (Hamilton Company, Reno, N.V.). Both ends of the tube were then dipped into separate 5 mL reservoirs filled with the same buffer. The end in which samples were introduced was connected with platinum electrodes to the positive high voltage. The reservoir at the detector was connected with platinum electrodes to ground. Samples were introduced either by electroinjection or by siphoning. The migration time $t_O$ of an uncharged species was determined from the solvent peak or injection of a trace of methanol. The migration time $t_{mc}$ of the micelle was determined by addition of the dye Sudan III to a micelle solution. The dye was assumed to be fully partitioned within the micelle, so that measurement of the migration time of the dye corresponded to $t_{mc}$.

Before each run, the capillaries were purged with 100 $\mu$L of 0.1M NaOH followed by 250 $\mu$L of triply distilled water. Care was taken to equilibrate the capillary with buffer prior to electroosmotic operation. The reproducibility of retention was better than 1% relative standard deviation from run-to-run and better than 3% from day-to-day. Moreover, it was found that reproducibility remained at 3% from capillary tube to capillary tube within the same batch of fused silica capillaries.

Experiment 1

Figure 3:
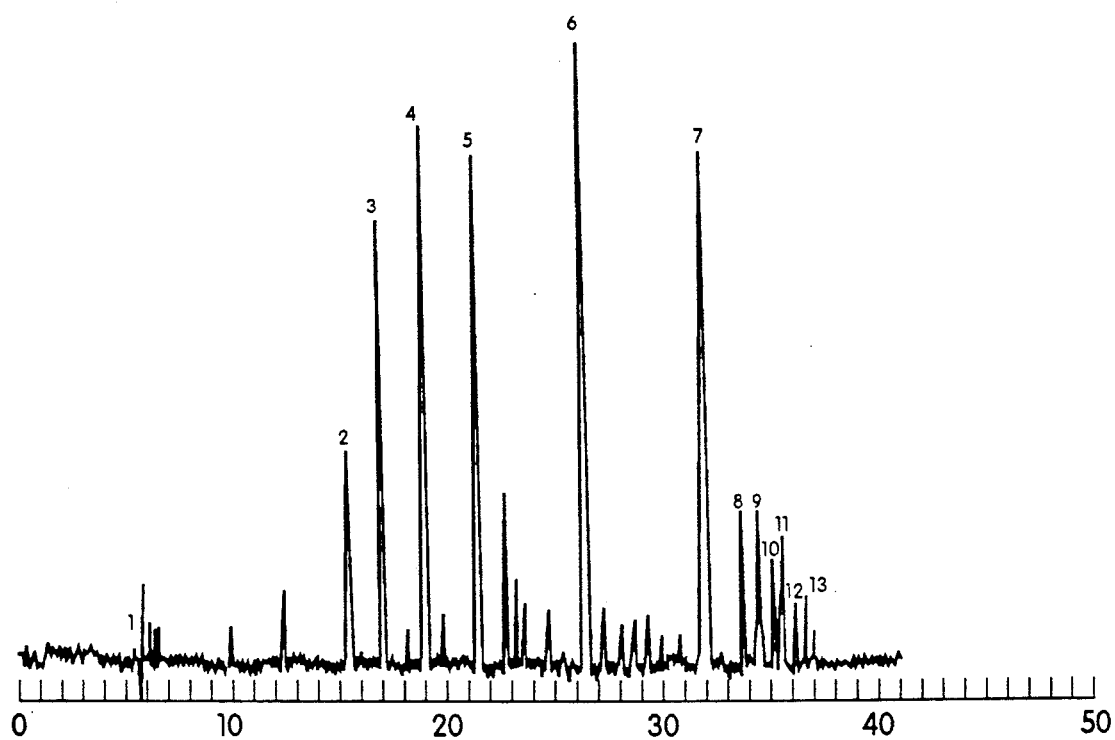
FIG. 3 shows an electropherogram of a polythymidine mixture the constituent oligonucleotides of which contain from 2–18 bases, using copper(II) for modifying the colloidal surface.

A 650 mm×0.05 mm ID capillary having an effective length to the detector of 450 mm was prepared containing 7M urea, 5 mM tris buffer, 5 mM $Na_2HPO_4$, 0.3 mM Cu(II) and 50 mM SDS, pH 7, thermostated at 25° C., and attached to a detector sensitive to a wave length of 260 nM. Applied voltage was 20 kV and the observed current was 10 $\mu$A. mixture of deoxypolythymidines was injected as described above and allowed to separate under the influence of the applied field. Results are shown in FIG. 3, where the numbered peaks and their identities are as follows:

1: solvent;
2: $d(pT)_2$;
3: $d(pT)_3$;
4: $d(pT)_4$;
5: $d(pT)_6$;
6: $d(pT)_{10}$;
7: $d(pT)_{12}$;
8: $d(pT)_{13}$;
9: $d(pT)_{14}$;
10: $d(pT)_{15}$;
11: $d(pT)_{16}$;
12: $d(pT)_{17}$;

13: d(pT)$_{18}$.

Experiment 2

Figure 4:
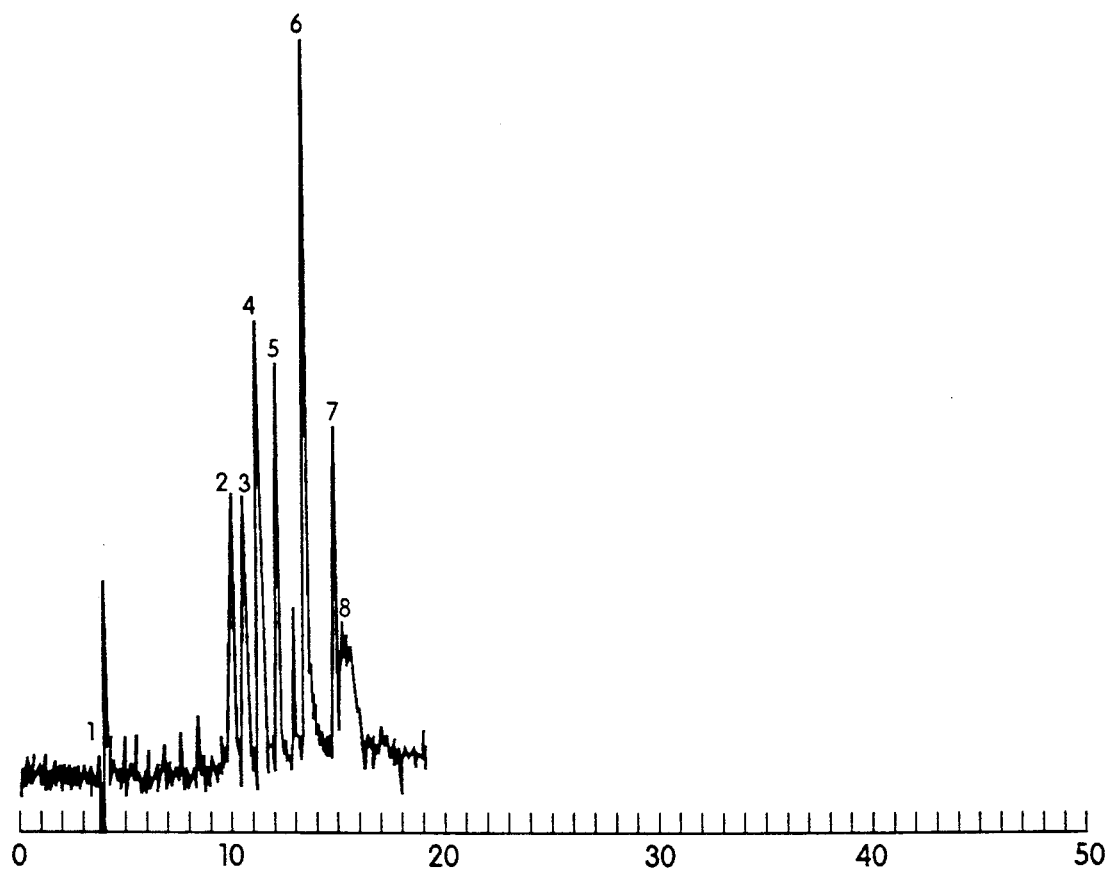
FIG. 4 shows a separation of the same polythymidine mixture as shown in FIG. 3, but using magnesium(II) in this case for modifying the colloidal surface.

The same mixture of polythymidines as was used in Experiment 1 was separated under the same conditions of capillary and instrumental parameters, with the exception that in this instance the capillary contained 5 mM Mg(II) instead of 0.3 mM Cu(II). Results are shown in FIG. 4, where the peaks and their identities are as follows:
1: solvent;
2: d(pT)$_2$;
3: d(pT)$_3$;
4: d(pT)$_4$;
5: d(pT)$_6$;
6: d(pT)$_{10}$;
7: d(pT)$_{12}$;
8: d(pT)$_{13}$-d(pT)$_{18}$.

Experiment 3

Figure 5:
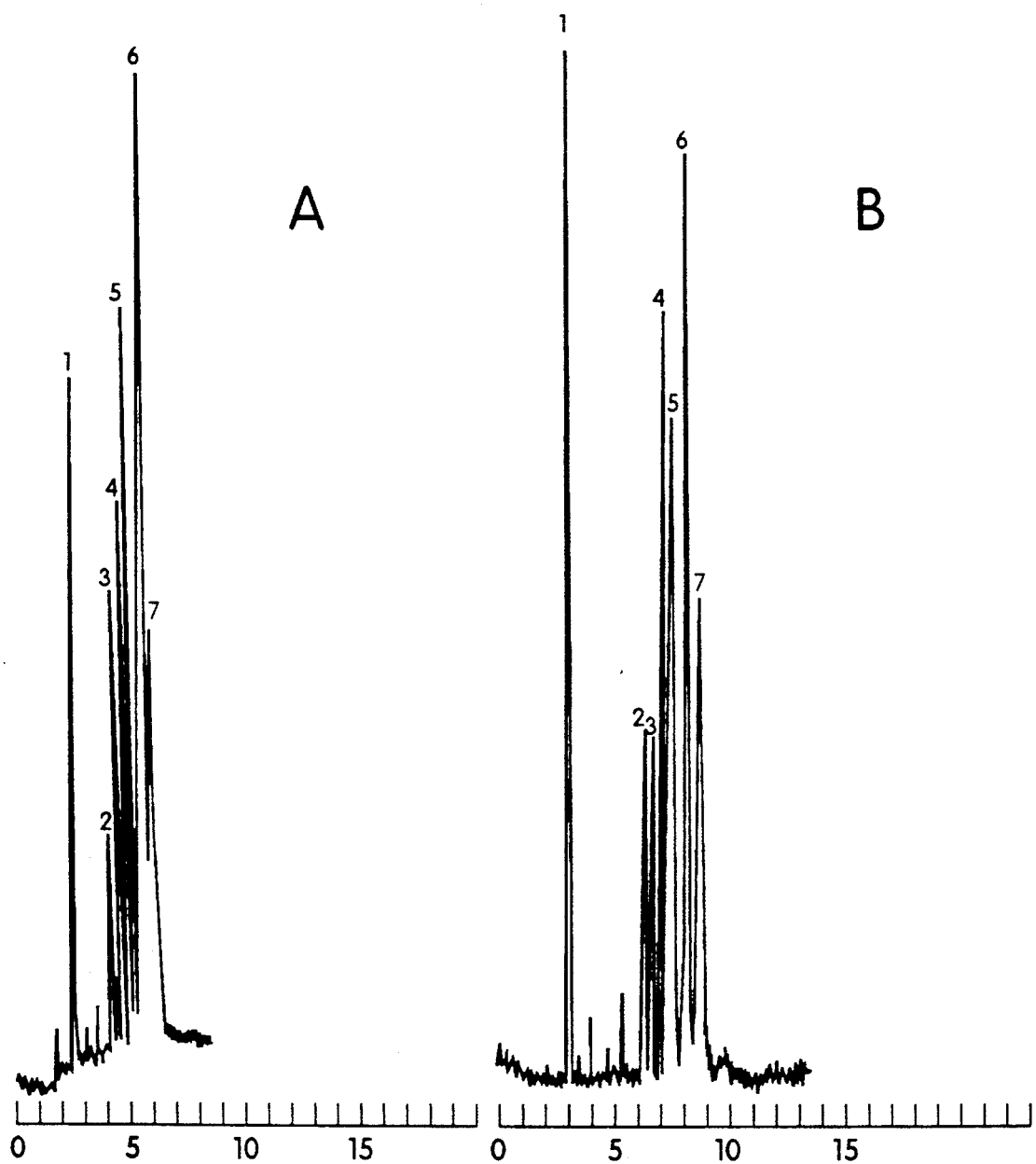
FIG. 5A shows a standard electrophoretic separation of the same polythymidine mixture as shown in FIG. 3, without the use of any colloidal material or surface-modifying complexing agents.
FIG. 5B shows an electrophoretic separation of the same polythymidine mixture shown in FIG. 3, employing as colloidal particles micelles of sodium dodecyl sulfate, but without any surface-modifying complexing agents being present.

The same mixture of polythymidines as was employed in Experiment 1 was separated under the same conditions as were used in Experiment 1 except that no sodium dodecyl sulfate and no metal ions were employed. Results are shown in FIG. 5A, where the numbered peaks are identified as follows:
1: solvent;
2: d(pT)$_2$;
3: d(pT)$_3$;
4: d(pT)$_4$;
5: d(pT)$_6$;
6: d(pT)$_{10}$;
7: d(pT)$_{12}$-d(pT)$_{18}$.

Experiment 4

The same mixture of polythymidines as was employed in Experiment 1 was separated under the same conditions as were used in Experiment 1 except that no metal ions were used. The results are shown in FIG. 5B, in which the numbered peaks are the same as those identified in FIG. 5A. FIGS. 5A and B, considered in relation to FIGS. 3 and 4, show that the combined use of micelles and metals improves the separations of the subject polythymidines very substantially.

Experiment 5

Figure 6:
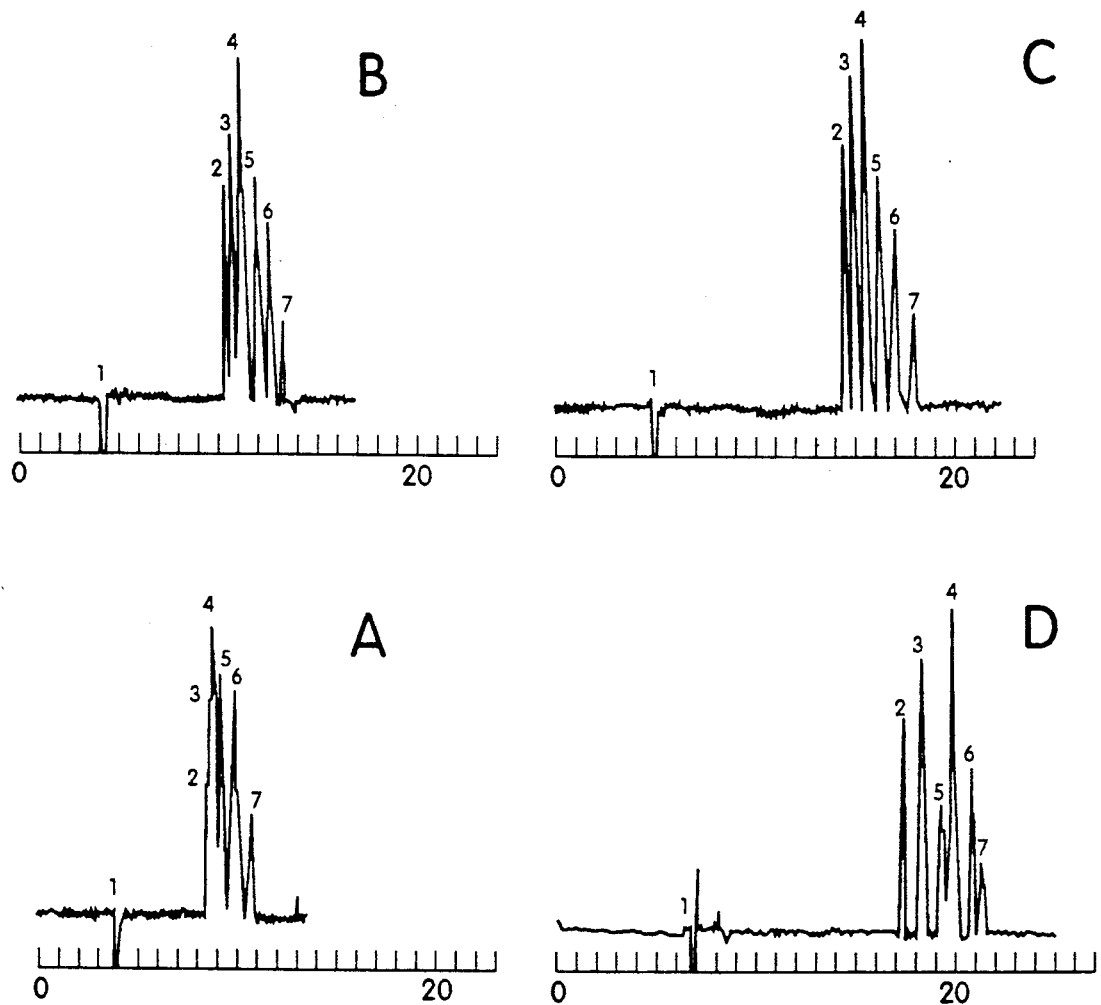
FIG. 6 shows the separation of a mixture of oligonucleotides, each of which contains 8 bases, as a function of the complexing agent employed in modifying the colloidal surface.

A mixture of 6 oligonucleotides each contained 8 bases was separated on the same sort of column and under the same conditions as were employed in Experiment 1 except that the buffer container 20 mM tris instead of 5 mM tris, and different amounts of the various metal ions were employed. The results are shown in FIG. 6, where FIG. 6A illustrates the separation with no metal ions, FIG. 6B results from the addition of 3 mM Mg(II) to the buffer, FIG. 6C results from the addition of 3 mM Zn(II) to the buffer, and FIG. 6D results from the addition of 3 mM Cu(II) to the buffer. The numbered peaks are as identified as follows:
1: water;
2: CATCGATG;
3: AACGCGTT;
4: GGGATCCC;
5: AAAGCTTT;
6: CGGGCCCG;
7: CGCCGGCG.

Experiment 6

Figure 7:
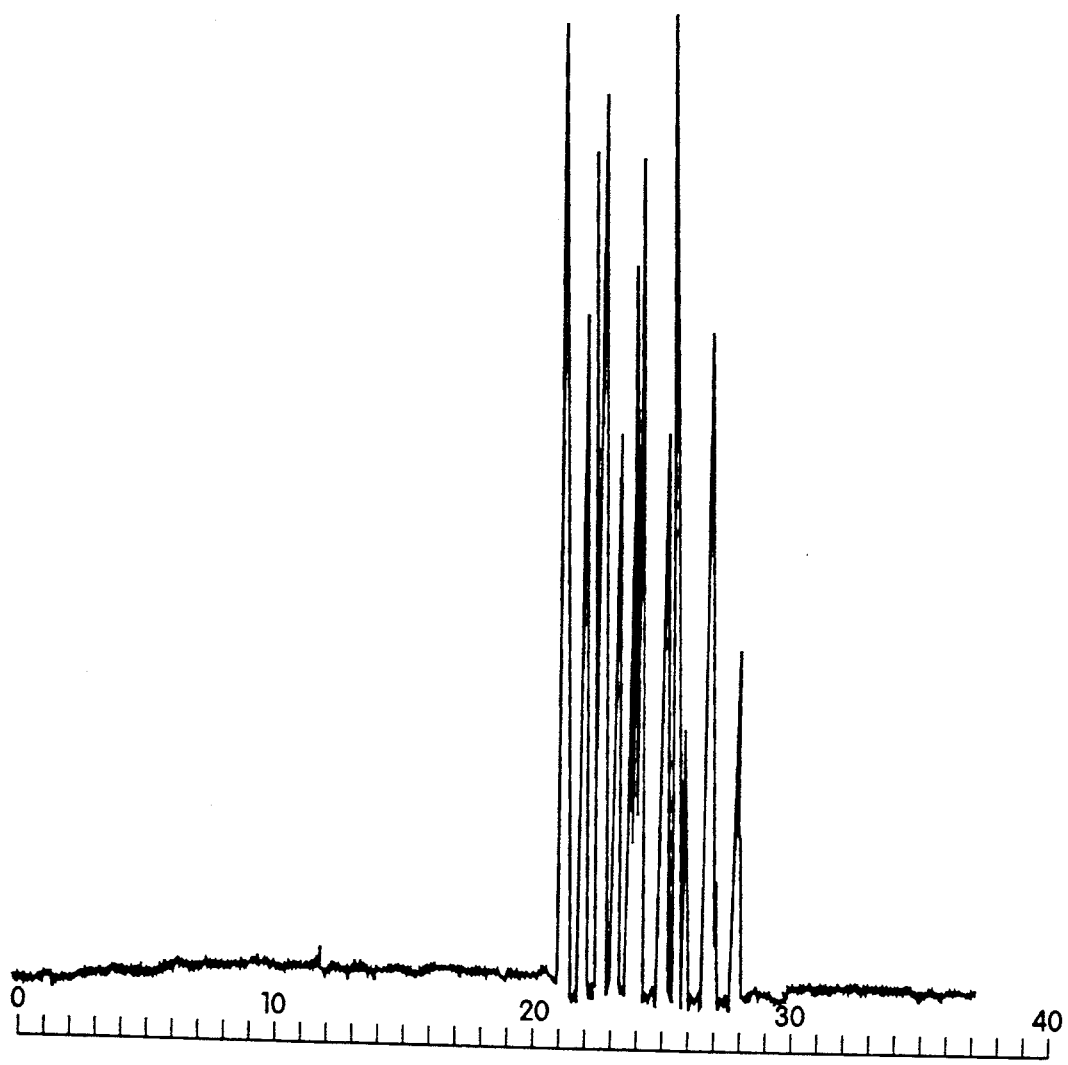
FIG. 7 shows the separation of a mixture of 18 oligonucleotides, each containing 8 bases, using the method and capillary of the invention.

An 850 mm × 0.05 mm ID capillary column having an effective length to the detector of 650 mm was prepared containing 7M urea, 20 mM tris, 5 mM Na$_2$HPO$_4$, 50 mM SDS, and 3 mM Zn(II). Applied voltage was 22 kV and the current was 52 μA. The system was thermostated at 25° C. and peaks were detected at a wave length of 260 nm as previously employed. A mixture of 18 oligonucleotides each containing 8 bases was injected and allowed to separate under the applied conditions. Results are shown in FIG. 7. Although the peaks are not identified, it is clear that an excellent separation of this exceedingly complex mixture has been achieved.

FURTHER EXAMPLES a) Negatively charged polystyrene latex particles are prepared by polymerization of styrene under a nitrogen atmosphere using potassium persulfate as initiator, then purified by dialysis and ion exchange. The negative charges on the particles result from fragments of the initiator. The polystyrene particles are mixed with an electrically-conductive buffer and the mixture is placed in a capillary tube, which is in turn connected to the electrophoresis apparatus discussed above and shown in FIG. 2. Those skilled in the art would be able to apply various approaches to stabilize the colloidal solutions. A sample containing one or more proteins is injected and an electric field is imposed. Depending on the ionic strength and the PH of the medium and the pI's of the proteins, the proteins will distribute themselves to various extents between the medium and the colloid surface. Separation is achieved by electrophoretic migration or electroosmotic flow, or both, and the separated materials are detected as they pass the detector. The proteins may be desorbed from the particles either on-line or off-line if desired, and may be collected as pure protein fractions.

b) Concanavalin A is covalently bound to the surface of colloidal particles of silica by a known procedure described in the Journal of Chromatography, 297, 167-177 (1984), which is hereby incorporated by reference. The concanavalin A is an affinity group which interacts specifically with α-linked mannose groups in materials such as glycoproteins and lectin. After this interaction, the particles remain charged. The surface-modified colloidal particles are mixed with an electrically-conductive buffer and the mixture is placed in a capillary tube, which is in turn connected to the electrophoresis apparatus described above and shown in FIG. 2. A sample containing one or more glycoproteins is injected and an electric field is imposed. The glycoprotein(s) will specifically adsorb to the colloid surface and will separate from the other materials present in the sample by electrophoretic migration, electroosmosis, or both, depending on whether the colloid and capillary are both charged or only one is charged. The separated materials are detected, and the glycoprotein(s) can be desorbed from the colloid particles either on-line or off-line, and collected.

c) The affinity group p-aminobenzamidine is covalently bound via a molecular spacer to hydrophobic particles of a polyvinyl polymer by a procedure given in the Journal of Chromatography, 292, 369-382 (1984) which is hereby incorporated by reference. This group interacts specifically with plasmin and plasminogen. Upon mixing the surface-modified colloidal particles in a buffer, filling a capillary tube with the resulting mixture, placing the tube in an electrophoresis apparatus, and injecting a sample containing plasmin and plasminogen, the plasmin and/or plasminogen will adsorb to the colloid. Upon application of an electric field plasmin-colloid and/or plasminogen-colloid complexes will be separated from other materials present in the sample, and detected after traversing the capillary. The adsorbed material is subsequently desorbed from the colloid, either on-line or off-line, if desired, and collected.

Other embodiments of the invention will be apparent to those skilled in the art from a consideration of this specification or the practice of the invention as disclosed herein. It is intended that the specification and examples be considered as exemplary only, with the true scope and spirit of the invention being indicated by the following claims.

What is claimed is:

1. An electrokinetic method of separating molecular species, employing the surface of colloidal particles, the method comprising the steps of:
   providing a dispersion of charged colloidal solid particles in an electrically-conductive medium in a capillary tube, said colloidal solid particles having a surface capable of interacting with at least one molecular species;
   placing into said dispersion an aliquot of a mixture containing a plurality of molecular species and including said at least one molecular species; and
   imposing an electric field across the length of said capillary tube;
   whereby said at least one molecular species distributes between the medium and the surface of the colloidal particles while traversing the capillary tube, separating from other molecular species in the mixture.

2. The method of claim 1 wherein said providing step further includes the step of modifying the original surface of said colloidal solid particles by incorporating thereon chemical functional groups.

3. The method of claim 1 wherein said providing step further includes the step of modifying the original surface of said colloidal solid particles by adding thereto metal ions.

4. The electrokinetic method of claim 3 wherein said metal ions are selected from the group consisting of ions of transition metals and alkaline earth metals.

5. The electrokinetic method of claim 3 wherein said metal ions are selected from the group consisting of ions of copper, iron, zinc, nickel, calcium and magnesium.

6. A capillary column for electrokinetic separation of molecular species employing the surface of colloidal particles, comprising:
   a capillary tube;
   an electrically-conductive dispersing medium; and
   colloidal solid particles having on their surface at least one material capable of interacting with molecular species to be separated;
   said colloidal solid particles and said dispersing medium being contained in said capillary tube.

7. The capillary column of claim 6 wherein said colloidal solid particles are selected from the group consisting of polystyrene, poly(vinylchloride), and silica.

8. The capillary column of claim 6 wherein said material capable of interacting with the molecular species to be separated is uncharged.

9. The capillary column of claim 8 wherein said material capable of interacting with the molecular species to be separated comprises an affinity group.

10. A capillary column for electrokinetic separation of molecular species employing the surface of colloidal particles, comprising:
    a capillary tube;
    an electrically-conductive dispersing medium; and
    negatively charged colloidal solid particles having on their surface positively charged ions of at least one metal capable of interacting with molecular species to be separated, and particles and said medium being contained in said capillary tube.

11. The capillary column of claim 10 wherein said negatively charged colloidal particles are selected from the group consisting of polystyrene, poly(vinyl chloride), and silica.

12. The capillary column of claim 10 wherein the positive metal ions on the surface of said colloidal solid particles are selected from the group consisting of transition metal ions and alkaline earth metal ions.

13. The capillary column of claim 10 wherein the positive metal ions on the surface of said colloidal solid particles are selected from the group consisting of ions of copper, iron, zinc, nickel, calcium and magnesium.

* * * * *